(12) United States Patent
Gregory, Jr et al.

(10) Patent No.: US 7,101,379 B2
(45) Date of Patent: Sep. 5, 2006

(54) RETRIEVAL BASKET FOR A SURGICAL DEVICE AND SYSTEM AND METHOD FOR MANUFACTURING SAME

(75) Inventors: Franklin P. Gregory, Jr, Racine, WI (US); Gregory Konstorum, Stamford, CT (US); Richard P. Muller, Bronx, NY (US); Frank D'Amelio, Los Olivos, CA (US); Gustave Jorgenson, Racine, WI (US)

(73) Assignee: ACMI Corporation, Southborough, MA (US)

( * ) Notice: Subject to any disclaimer, the term of this patent is extended or adjusted under 35 U.S.C. 154(b) by 62 days.

(21) Appl. No.: 10/013,005

(22) Filed: Nov. 5, 2001

(65) Prior Publication Data

US 2003/0088254 A1 May 8, 2003

(30) Foreign Application Priority Data

Apr. 2, 2001 (DE) .......................... 101 17 836
Oct. 5, 2001 (DE) .......................... 101 50 399

(51) Int. Cl.
*A61B 17/22* (2006.01)

(52) U.S. Cl. ....................................... 606/127
(58) Field of Classification Search .................. 606/113, 606/114, 127, 200
See application file for complete search history.

(56) References Cited

U.S. PATENT DOCUMENTS

| 4,198,960 | A |   | 4/1980  | Utsugi |
|-----------|---|---|---------|--------|
| 5,057,114 | A |   | 10/1991 | Wittich et al. |
| 5,064,428 | A |   | 11/1991 | Cope et al. |
| 5,344,427 | A | * | 9/1994  | Cottenceau et al. ........ 606/127 |
| 5,792,145 | A |   | 8/1998  | Bates et al. |
| 5,989,266 | A |   | 11/1999 | Foster |
| 6,224,612 | B1 |  | 5/2001  | Bates et al. |
| 6,267,776 | B1 | * | 7/2001 | O'Connell .................. 606/127 |
| 6,302,895 | B1 |  | 10/2001 | Gobron et al. |
| 2001/0001315 | A1 | | 5/2001  | Bates et al. |
| 2001/0041899 | A1 | | 11/2001 | Foster |
| 2002/0026203 | A1 | | 2/2002  | Bates et al. |
| 2002/0068944 | A1 | | 6/2002  | White et al. |
| 2002/0068954 | A1 | | 6/2002  | Foster |

FOREIGN PATENT DOCUMENTS

DE     24 04 058 B2   6/1979
WO     WO 98/36694    8/1998

\* cited by examiner

*Primary Examiner*—Kevin T. Truong
(74) *Attorney, Agent, or Firm*—Ganz Law, PC; Bradley M. Ganz; James L. Wolfe

(57) ABSTRACT

A medical retrieval basket device, comprising a plurality of basket wires forming a basket, the basket including a wire collector at its distal end, the wire collector having a substantially rigid body for receiving the wires, the wire collector securing the wires at the distal end of the basket so as to provide a substantially tipless basket.

89 Claims, 10 Drawing Sheets

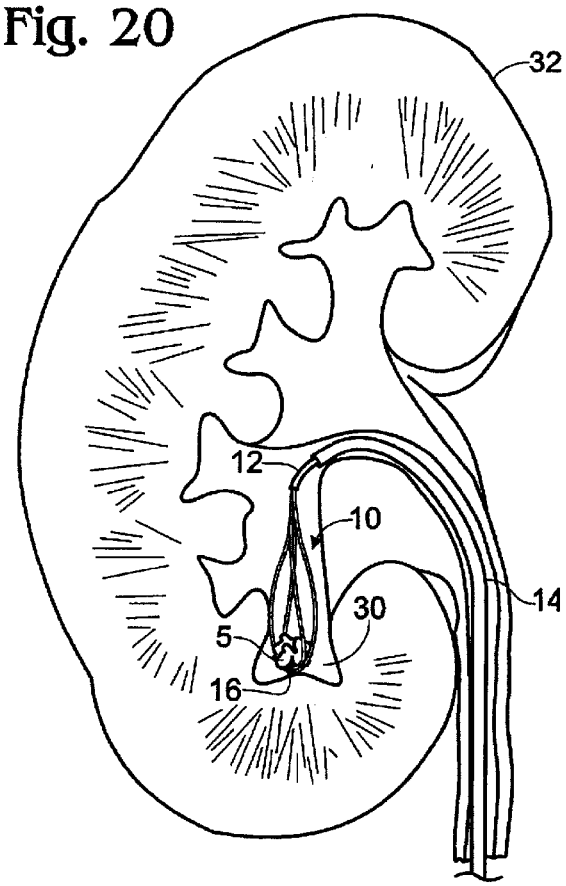
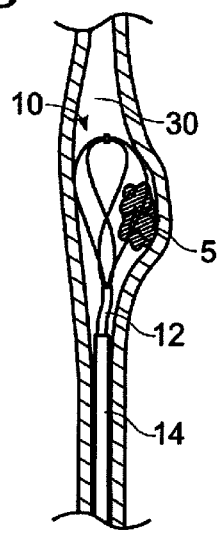
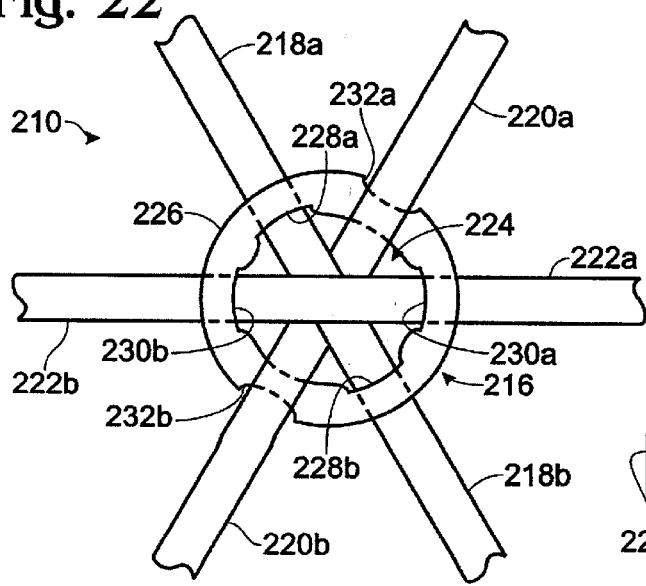
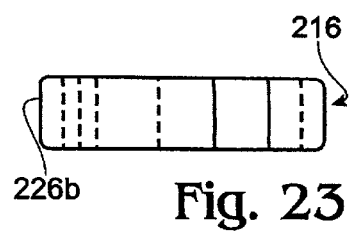

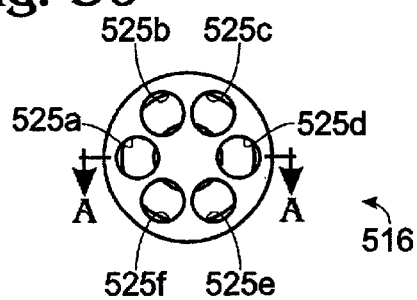
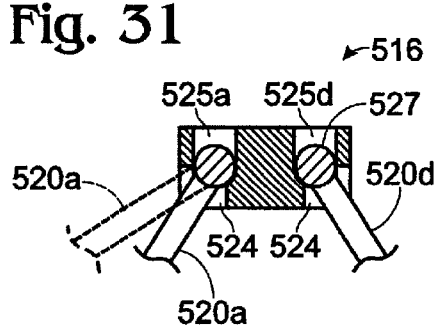
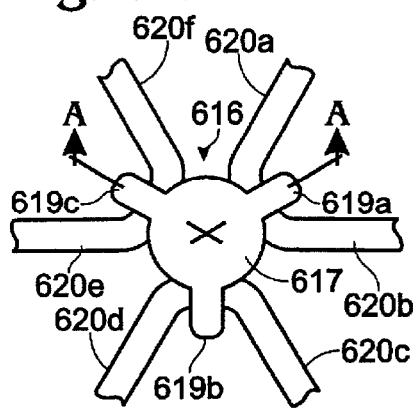
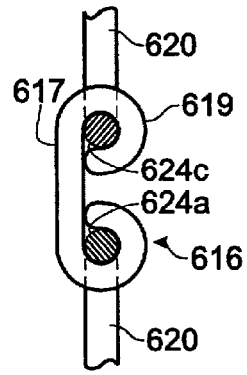
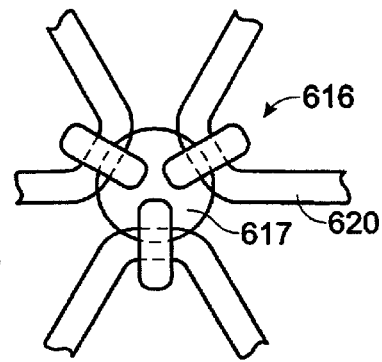
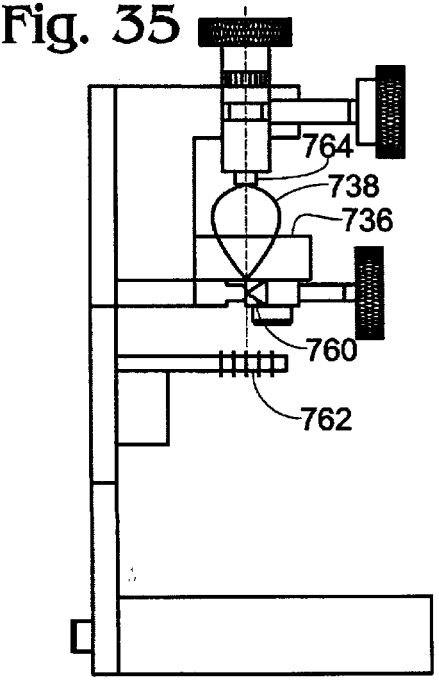

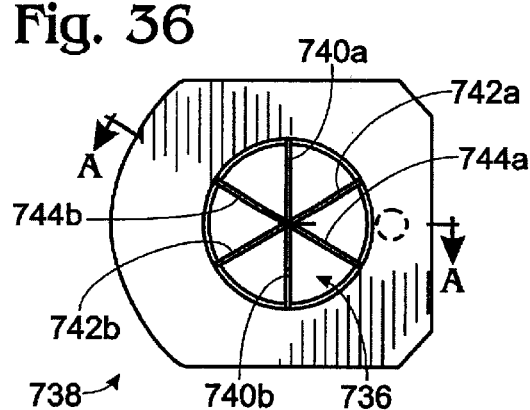
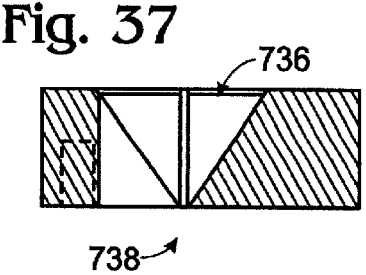
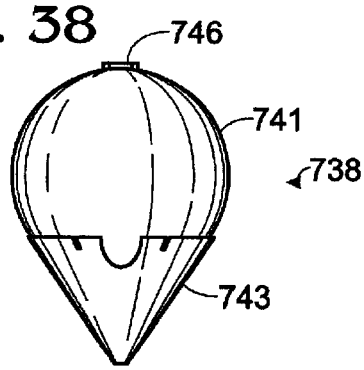
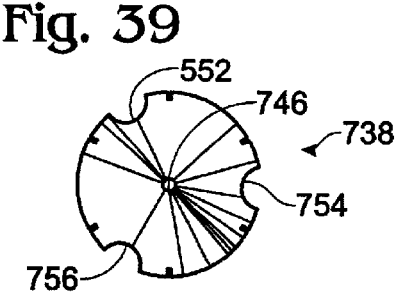
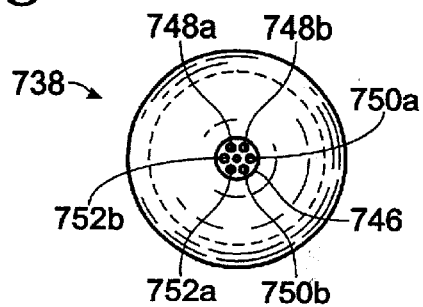
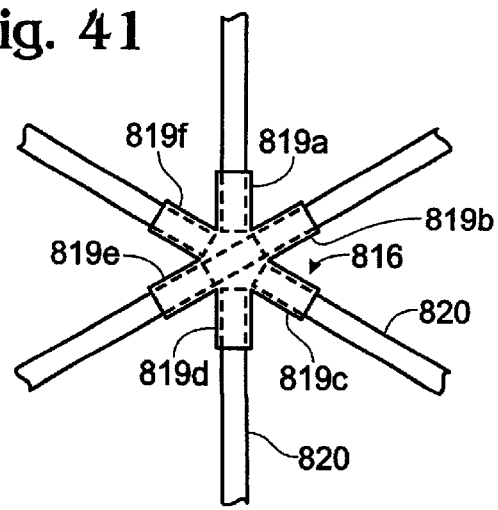

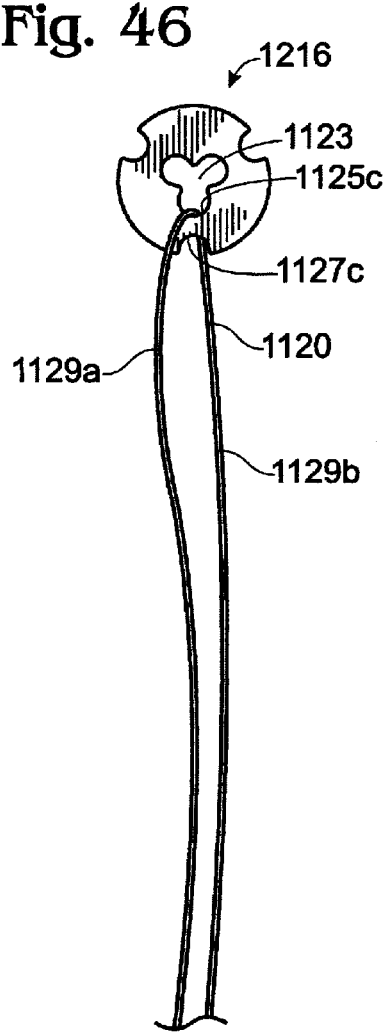
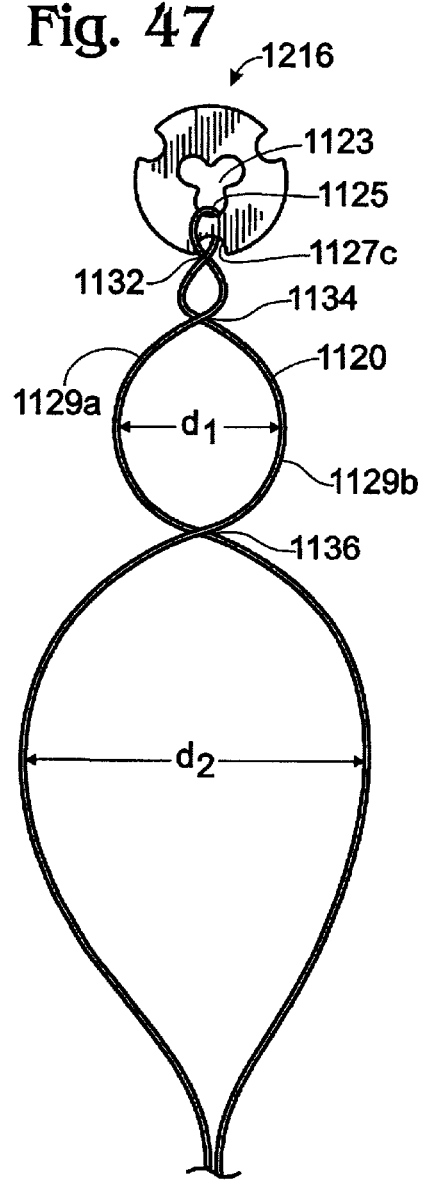

RETRIEVAL BASKET FOR A SURGICAL DEVICE AND SYSTEM AND METHOD FOR MANUFACTURING SAME

Applicants claim the benefit of co-pending German Patent Application Nos. DE 101 17 836.0, filed on Apr. 2, 2002, and DE 101 50 399.7, filed on Oct. 5, 2001.

FIELD OF THE INVENTION

This invention provides a retrieval basket for use in retrieving objects from a human or animal body. In particular, it provides a basket adapted to capture and remove calculi or other bodies from a human patient's body.

BACKGROUND OF THE INVENTION

There is an ongoing demand for improved surgical devices that are capable of removing objects from a patient's body. In the fields of urology and gastroenterology, for example, improved devices are needed for capturing and retrieving calculi (or "stones") formed in the urinary tract. Calculi deposits commonly are composed of calcium oxalate. Calculi cause pain, whether they are positioned in the kidney or bladder, or elsewhere, and they can be especially painful as they pass through a duct, such as the ureter. Calculi often need to be removed surgically to alleviate pain, urinary obstruction, or possible infection.

Various retrieval baskets have been proposed over the years for calculi removal. They generally include wires formed to define a "cage" in an expanded position into which calculi can be maneuvered. A sheath may be provided to maintain the wires in a collapsed position for insertion. A handle may be provided for manipulation of the sheath and basket with respect to one another in order to move the basket or cage between the collapsed and expanded positions. A conventional helical style basket is typically used for capturing calculi from the patient's duct, while a conventional straight wire basket is typically used for capturing calculi from the patient's Kidney calyx.

For patient duct calculus retrieval's, the basket is advanced distally to a position within the patient's duct that is beyond a calculus to be grasped while the basket is in the collapsed position within the sheath. It is subsequently expanded upon release from the sheath and drawn back proximally to capture the calculus.

For kidney calyx calculus retrieval's, the basket is advanced to a position within the patient's kidney just proximal to the calculus while the basket is in the collapsed position within the sheath. The basket is subsequently expanded upon release from the sheath, advanced into the calculus, and if necessary, rotated using device handle) to capture the calculus.

Conventional retrieval baskets typically have wire members that are gathered and fastened together into a tube forming a tip extension 2. The tip extension follows the long axis of the basket. An example of a conventional straight wire device with an extended tip is shown in FIGS. 1 and 2. Conventional devices have a tip extension distance d typically of 5–8 mm. The rigid tip extension 2 may cause patient discomfort, bleeding—which not only may be injurious, but can blur the physician's working field of vision—or patient trauma when advanced into certain kinds of tissue, including mucosal tissue. The extending tip is also a design disadvantage in many stone capture attempts (especially for calyceal stones) because the extended tip encounters structures so that basket wires are hindered or prohibited from reaching the distal side of the stone.

In addition to the disadvantages of an extended tip, conventional means for securing the distal end of a basket may hinder the operation of the basket. For example, the opening and closing of the basket wires may be suboptimal, depending on how the wires are secured to form the distal end of the basket.

In the prior art, attempts have been made to provide tipless baskets. Wittich, et al., U.S. Pat. No. 5,057,114 and Cope, et al., U.S. Pat. No. 5,064,428 each disclose a basket without an extending tip. Wire loops in the basket are secured together at their distal end via a suture treated with a urethane coating material. Foster, U.S. Pat. No. 5,989,266 also discloses a basket without an extending tip. In this case, a small wire loop is formed in a first of two larger basket wires. At the distal end of the basket, the second of two wire loops passes through the smaller loop to interlock the larger wire loops together and to form a tipless basket. Accordingly, apart from sutures and wires, the tipless baskets of the prior art do not involve any structural body combined with wires. Given reliability and safety issues inherent in medical procedures, there is a strong demand for tipless retrieval devices that have improved strength and integrity.

There are significant disadvantages in the foregoing approaches for forming a tipless basket. For example, the wires at the distal tip are either self-securing or secured by suture materials. These methods provide baskets of questionable strength and/or integrity. Further, the tipless devices of the prior art may be prone to rapid wear or degradation in use or in sterilization procedures (if the device is a non-disposable). Further, the use of interlocking wires may compromise the shape and integrity of the basket because the wires may move relative to each other given the nature of a loop or suture. The process of assembling the basket may also be complicated by the nature of the foregoing construction and materials. For example, the foregoing tipless prior art baskets are not known to be suitable for use in helical wire baskets. Helical baskets provide improved grasping and release functionality relative to convention basket arrangements. It is questionable whether the looping or suturing methods would be suitable for forming and maintaining the demanding configuration of a helical basket. Further, the foregoing tipless prior art baskets are known to have difficulty capturing and retaining calculus. Accordingly, there is a need for tipless baskets that provide improved grasping, retention and release functionality relative to conventional basket arrangements. For at least the foregoing reasons, there is a need for improved means of securing the distal ends of a medical retrieval basket. More particularly, there is a need for improved tipless retrieval baskets.

SUMMARY OF THE INVENTION

The present invention provides an improved retrieval basket that overcomes the drawbacks of conventional baskets, including the disadvantages of known tipless baskets. Among other things, the present invention provides a retrieval basket that captures objects such as calculi securely, yet it may also release captured objects, if desired. In certain embodiments, the present invention provides a basket with a distal end having a minimal standoff distance.

In certain embodiments, the present invention provides a universal application basket which overcomes the anatomically restrictive calculus retrieval limitations of prior art baskets.

The present invention may be used to capture and remove impacted stones from body passages. In certain embodiments, the present invention provides a basket with helically pathed wires that affords better stone ingress and retention capability.

In certain embodiments, the present invention provides a basket that affords improved rotatability and positionability in a body passage.

The present invention also provides a basket that has a reduced risk of pain, bleeding or trauma to tissue.

More particularly, the present invention provides the following general embodiments:

A medical retrieval basket that includes a plurality of basket wires forming a basket. A wire collector with means for receiving each basket wire is disposed on the distal end of the basket, the wire collector having a substantially rigid body. The wire collector receives the wires in the receiving means so as to provide a substantially tipless basket.

A medical retrieval basket that includes a plurality of basket wires forming a basket. A wire collector with means for receiving basket wires is disposed at the distal end of the basket, the wire collector having a substantially rigid body. The wire collector receiving means receives the wires in an orientation that is substantially non-parallel to the long axis of the basket when the basket is in its open position.

A medical retrieval basket that includes a plurality of basket wires forming a basket, a shaft extending proximally of the basket, and a wire collector with means for receiving basket wires disposed at the distal end of the basket, the wire collector having a substantially rigid body, and the receiving means receiving the wires in an orientation that is substantially non-parallel to the long axis of the basket when the basket is in its open position.

A medical retrieval basket that includes a plurality of basket wires forming a basket, and a wire collector with means for receiving basket wires disposed at the distal end of the basket, the wire collector having a substantially rigid body and receiving the wires so as to provide a substantially tipless basket.

A medical retrieval basket that includes a plurality of basket wires forming a basket for capturing a target body and a shaft attached proximally thereto, the basket including a wire collector at its distal end, the wire collector having a body with a plurality of wire receiving means that help define the shape of at least a distal portion of the basket. At least two basket wires form a pair extending along helical paths, the pair of wires being closely spaced and adjacent in a proximal region of the baskets, radially diverging in an intermediate region of the basket, and radially converging in a distal region of the basket into the wire collector.

A medical device that includes a basket and sheath, the basket being retractable into the sheath, the basket device having a plurality of basket wires forming a basket, the basket including a wire collector at its distal end, the wire collector having a body receiving and securing basket wires at the distal end of the basket so as to provide a substantially tipless basket, wherein the wires have a substantially round cross section or other desired cross section.

A method of forming a basket for a retrieval basket that includes steps of providing a wire collector having a plurality of wire receiving means, placing wires in the receiving means, and providing a form representing a desired basket shape, the form including positioning means for setting the wires in a predetermined position; arranging wires around the form; and fixing one or both ends of the wires in the basket so that they are secured together and define a basket; and removing the form.

A form representing a desired retrieval basket shape, the form having wire positioning means for receiving and setting a plurality of basket wires in a predetermined position, the form including means for receiving and positioning a wire collector.

Other specific embodiments and advantages of the present invention will become clear in view of the following description.

BRIEF DESCRIPTION OF THE DRAWINGS

FIG. 20 shows a retrieval basket according to the present invention being used to capture a lower pole calyx stone from a kidney.

FIG. 21 shows a retrieval basket according to the present invention being used to capture a stone impacted in a ureteral wall.

FIG. 22 shows a front elevation (distal end) view of an alternative embodiment of a wire collector and collected wires according to the present invention.

FIG. 23 shows a side elevation view of the wire collector of FIG. 22.

FIG. 30 shows a top (distal) view of another embodiment of a wire collector according to the present invention.

FIG. 31 shows a sectional view taken along line A—A in FIG. 30.

FIG. 32 shows a top (distal) view of an alternative embodiment of a wire collector according to the present invention.

FIG. 33 shows a side elevation view of a wire collector taken along line A—A in FIG. 32.

FIG. 34 shows a bottom view of the wire collector shown in FIG. 32.

FIG. 35 shows a side view of an apparatus for manufacturing a surgical basket in accordance with the present invention.

FIG. 36 shows a top view of a component included in the apparatus of FIG. 35.

FIG. 37 shows a side sectional view taken along line A—A in FIG. 36.

FIG. 38 shows a side view of a component used with the apparatus of FIG. 35.

FIG. 39 shows a bottom view of the component of FIG. 38.

FIG. 40 shows a top view of the component of FIG. 38.

FIG. 41 shows a top (distal) view of another embodiment of a wire collector and wires according to the present invention.

FIG. 45b shows a side view of the wire collector of FIG. 45a.

FIG. 46 shows the embodiment of FIG. 45 with a length of wire for forming a basket.

FIG. 47 shows the embodiment of FIG. 46 after configuring the basket wire.

DETAILED DESCRIPTION OF THE INVENTION

This invention relates to surgical devices for extraction of a "target body" such as calculi or other natural or foreign body from a duct, tract, cavity, channel or other such area of a patient's body. (Hereinafter "duct", "tract", "cavity", "channel" or other such area of a patient's body may be referred to simply as a "channel"). This invention is described in reference to certain possible embodiments shown in the Figures. However, the invention is not limited to these embodiments, and the illustrations are not intended to conform to any particular scale. As will be apparent from the discussion that follows, the inventive subject matter can be implemented into a variety of basket arrangements in terms of shapes of baskets, number of wires in a basket, and the paths taken by wires in a basket. For example, a basket can be formed from any number of wires, depending on the intended usage of the basket; size limitations dictated by the usage; and manufacturing and cost considerations. The baskets of the present invention are resiliently collapsible such that the basket expands into an open position automatically when deployed from a surrounding sheath and collapses when drawn into the sheath.

The present invention provides a novel means for collecting basket wires at the distal end of a basket. One basic novel concept of the present invention is to provide a "wire collector" having a body that receives wires in a manner that does not substantially extend the wires distally of the basket profile and/or does not extend the body beyond the distal profile of the basket. This may be achieved by providing receiving means on the body that gather the wires at an acute or obtuse angle to the long axis of the basket. This may also be achieved by providing termination points on the body for the wires so that the wires are extended such that they do not extend distally of the basket profile.

In contrast to the prior art suture and wire means for forming a tipless basket, and the inherent disadvantages of such devices, the body of the wire collector is a substantially rigid structure that provides integrity to the basket and/or a means for securely orienting and/or fastening wires to help define and maintain the same and functionality of the basket. Specific examples of wire collectors in accordance with the present invention are discussed below.

Figure 1:
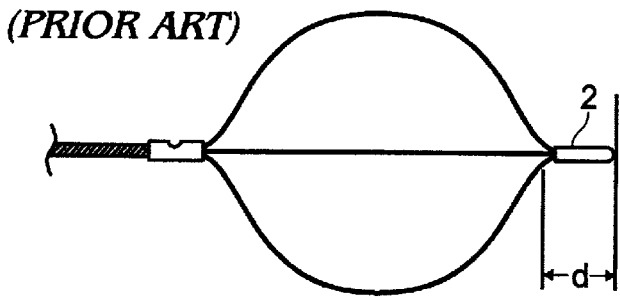
FIG. 1 shows a side elevation view of a retrieval basket, with an extended tip on the right (distal) side, and a section of basket shaft, according to the prior art.
Figure 2:
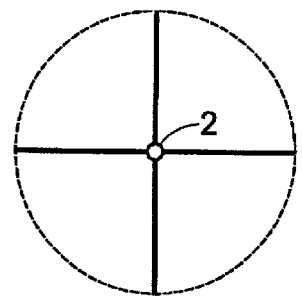
FIG. 2 shows a front elevation (distal end) view of the prior art device of FIG. 1.
Figure 3:
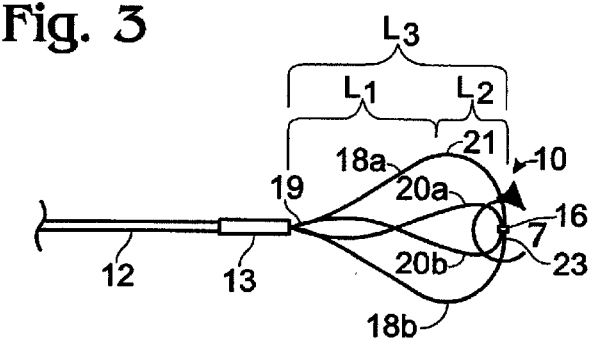
FIG. 3 shows a side elevation view of a four-wire retrieval basket representing one of many possible embodiments of the present invention.
Figure 5:
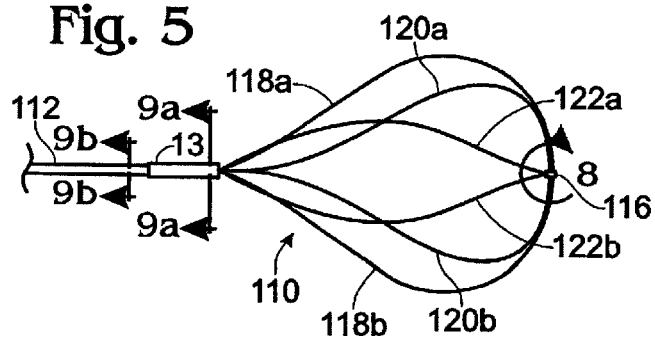
FIG. 5 shows a side elevation view of a six-wire retrieval basket of the present invention.

FIG. 3 shows one of many possible embodiments of the present invention that illustrates both of the foregoing principles. The discussion of embodiment of FIG. 3 applies to the corresponding features in the embodiment of FIG. 5. Like numerals are used to indicate like features in FIGS. 3 and 5, as well as other embodiments described herein. For example, 18, 118, and 218 all refer to basket wires. Significant differences among the embodiments are noted. FIG. 3 shows a basket with four basket wires 18a, 18b, and 20a, and 20c defining a basket 10. FIG. 5 shows a basket with six basket wires 120a, 120b, 122a, 122b, 124a and 124b, defining a basket 110. A retrieval basket device is generally an assembly of a basket 10/110 and a shaft 12/112 that is connected to the proximal end of the basket. (Where FIG. 3 and FIG. 5 have corresponding features, slashes may be used to separate reference numerals for corresponding features.)

The assembly would also generally include a sheath 14 (See FIGS. 14–21) or other tube-like structure for slidably housing and deploying the basket and shaft.

Basket 10 has a longitudinal axis that extends through the center of the basket between the proximal and distal ends of the basket. In FIG. 3, basket 10 is shown in an unsheathed, expanded position. The basket is resiliently collapsible for retraction into a sheath or other restraining means. In the expanded position, the basket has a distal portion with a hemispherical shape and a proximal portion with a triangular shape. The combination of these portions creates an overall pear-like basket shape. Other configurations are within the scope of the invention.

The proximal portion of basket 10 has a length $L_1$ between its proximal end at a proximal basket wire convergence point 19 and a basket wire maximum 21. Maximum 21 is the point along a wire where it has maximum divergence radially from the longitudinal axis of the basket. A distal portion of basket 10 has a length $L_2$ between maximum 21 and a distal basket, wire convergence point 23, which is the distal end of basket 10. The retrieval basket has an overall basket wire length $L_3$ from proximal basket wire convergence point 21 to distal basket wire convergence point 23. $L_1$ is greater than $L_2$ in the embodiments of FIGS. 3 and 5. Proximal of the basket is a trailing region behind where the wires of the basket come together to form the proximal end of the basket. The trailing region is a shaft or shaft-like element. The trailing region may be connected or integrated to a shaft, or may be part of the shaft, as described below.

Figure 4:
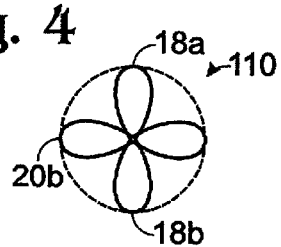
FIG. 4 shows a front elevation (distal end) view of the retrieval basket of FIG. 3.
Figure 6:
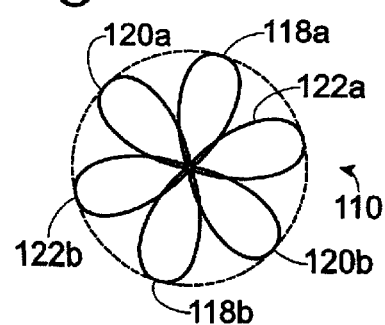
FIG. 6 shows a front elevation (distal end) view of the retrieval basket of FIG. 5.

In one of many possible embodiments, two basket wires form a pair. Each wire in the pair follows an opposing helical path, going from the proximal end of the basket to the distal end. The embodiment of FIG. 3 shows two pairs of wires, 18a–b and 20a–b in such paths. In the embodiment of FIG. 6, there are three pairs of wires, 118a–b, 120a–b, and 122a–b in such paths. In another possible embodiment, one or more wires extend along so-called "dual helical paths" wherein each wire extends along a proximal helical path and then along a distal helical path that has a smaller radius of curvature compared to the proximal helical path. Preferably, the dual helically-pathed wires are in one or more pairs, with the wires in a pair following mirror image paths. Examples of such pairs are wire pairs 18a–b and 20a–b in FIGS. 3–4, wire pairs 118a–b, 120a–b, and 122a–b in FIGS. 5–6, and wire pairs 218a–b, 220a–b, and 222a–b in FIG. 22. The basket wires 18a–b and 20a–b follow helical paths to define the aforementioned proximal and distal portions of basket 10. Because helical paths are followed, the wires lie in different planes, as seen in FIG. 4. This creates a basket with four basket wires that appear in FIG. 4 as four lobes spaced every 90°. In FIG. 6, there are six lobes spaced every 60°. The circumferential gaps between lobes represent good areas for ingress and capture of a target body.

In the proximal basket portion, the basket contains adjacent wire members, e.g., 18b, 20a that first lie on closely spaced helical paths. A basket formed of such wires provides a high radial opening force, as required for stone retrieval from a vessel (i.e., ureter). The radial opening force should be sufficient to dilate the ureter or other body channel for better access and capture of a stone or other target body. Preferably, after an initial section of being closely adjacent, wires 18b and 20b diverge circumferentially from each other, providing larger gaps for optimum stone ingress towards the basket midsection and distal portion, as required in stone retrieval from cavity anatomy (i.e., kidney, calyx, renal pelvis, bladder or gallbladder). (These gaps can be seen as the spaces between basket wire lobes in FIGS. 4 and 6.)

The present invention is not intended to be limited to baskets having wires following helical paths, other configurations are within the scope of the invention, as will be apparent to persons skilled in the art from the teachings herein. Likewise, the principles of the present invention may be applied to baskets where the wires follow the same or different paths that may or may not match that of other wires in the basket. Further, the basket can have an odd number of wires although an even number is preferred.

The basket wire members are preferably of medium stiffness. A preferable wire material shape memory alloy. Nickel-titanium based alloys, such as Nitinol, are suitable and available from various commercial sources. Other suitable wire materials include other shape memory material or alloy; a work-hardened 300 series stainless steel; or a chromium cobalt alloy. Sufficiently rigid thermoset or thermoplastic materials may also be used. Shape memory plastics, such as shape memory polyurethanes, may also be suitable. The basket wires used to form a basket preferably have a round, substantially round, or other smooth cross section. One advantage of a round or smooth cross section is that it reduces the risk of trauma to tissue. Four- or six-wire baskets having a radial circumference of about 10-mm to about 20 mm, a Nitinol wire of about 0.006" diameter are suitable for use in removing calculi from the urinary tract.

Figure 7:
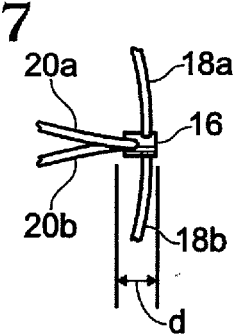
FIG. 7 is an enlarged side elevation view of the portion of the retrieval basket from FIG. 3, taken along curved line 7 in FIG. 3.
Figure 8:
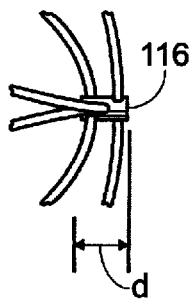
FIG. 8 is an enlarged side elevation view of the portion of the retrieval basket from FIG. 5, taken along curved line 8 in FIG. 5.

The wires 18a–b and 20a–b forming basket 10 are distally collected in a novel wire collector 16. Advantageously, wire collector 16 may be used to collect wires 18 and 20 without creating a tip that extends substantially beyond the distal end 23 of basket 16. As seen in FIG. 7, the distal end of wire collector 16 is substantially coextensive with the distal end of the basket defined by four wires 18a–b and 20a–b. A single length of wire may be used to form a basket wire pair, such as wire pair 18a–b (collectively designated 18) or wire pair 20a–b (collectively designated 20). A wire collector according to the present invention is not limited to any particular number of basket wires, basket shape, or wire materials.

Figure 10:
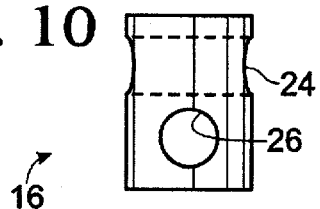
FIG. 10 shows a side elevation view of a wire collector for a four-wire basket according to the present invention.

FIG. 10 shows wire collector 16 in more detail. Wire collector 16 is a body with wire receiving means. Wire collector 16 includes wire receiving means for collecting, organizing, and securing the wires at the distal end of the basket. The receiving means may also provide means for a wire to hinge or otherwise move to facilitate opening or closing of a basket formed using the wire. The wire receiving means may be disposed in the body of the wire collector so as to capture or direct the wires in a manner that produces a basket with little or no extending tip. Preferably, to help provide a tipless basket, the wires are received in an orientation that is generally perpendicular to the long axis of the basket when the basket is in its open position. Thereby, there does not need to be any structure extending distally beyond the distal profile and the basket, in this case, the points where the wires are received on or in the wire collector. The wire receiving means may be full or partial passages in the wire collector. The wire receiving means may also be welds, bonding, fasteners, or other surface connections. The embodiment of FIG. 10 includes receiving means in the form of passages 24 and 26 for receiving wires 18 and 20. In this embodiment, the passages extend through a wire collector having a solid body. In the embodiment shown, the wire collector has a generally elongate, cylindrical shape, although other shapes are possible.

Figure 11:
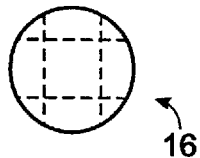
FIG. 11 shows a top elevation view of the wire collector of FIG. 10, with passages provided in the wire collector shown in phantom.

The passages 24 and 26 lie in different planes, with passage 24 lying distally above passage 26. As seen in FIG. 11, passages 24 and 26 are relatively transverse to each other. The passages receive a length of wire 18 or 20 and the orientation of the passages helps define the shape and ending of at least the most distal portion of basket 10. In the embodiments shown, a basket wire 18*a* or 20*a* passes through a passage 24 or 26 and is returned from the distal end of the basket to the proximal as wire 18*b* or 20*b*. Of course, the reference to one wire being received and the other being returned is arbitrary, with vice versa designation possible. To better secure the wires in the wire collector, there may be a close friction fit of the wires in the passages of the wire collector. Also for better securing the arrangement of wires in the wire collector, the wire collector may optionally be crimped to fix the wires in place. The wires and body may also be formed as an integral unit, i.e., as a one-piece unit of a single or multiple materials.

In one possible embodiment, shown in FIG. 10, suitable for urological and other minimally invasive endoscopic applications, wire collector 16 has a stainless steel body with a length of about 0.025" and a diameter of about 0.016". Passages 24 and 26 have a diameter of about 0.0075". Passages are spaced above each other and transverse (90°) to each other. The distance between centers of adjacent passages is about 0.01". The embodiment of FIG. 12 has similar dimensions but has a longer length, totaling about 0.36", to accommodate an extra passage. In this case, the passages are offset at an angle of 60°.

It is also contemplated that the wires going to a wire collector 16 or 116 may terminate in the wire collector instead of passing therethrough. In such an embodiment, the passages 24, 26, 124, 126, or 128 do not extend completely through the body of the wire collector. As noted above, it is also contemplated that a wire collector might not have any passages. Instead, other securing means could be provided to attach the basket wires to the wire collector such as soldering, welding or other bonding means. As one possible example, wires may be junctioned as desired to form the distal end of a basket. The junctioned wires do not necessarily need to be in contact with each other; they could just be closely arranged together. Next, a bonding agent, such as a known epoxy bonding material or metal solder, is disposed over the junction of the wires to form a wire collector, such as 16 or 116, but without the passages. As another example, the wire collector and wires may be cast or extruded in place, or they may be surface welded to the body of the wire collector.

In addition to the novel wire collectors already described, the present invention contemplates other embodiments of wire collectors that may be used to form a tipless basket. FIGS. 22 and 23 show one example of a novel alternative embodiment. In this embodiment, wire collector 216 receives basket wires 218*a*, 218*b*, 220*a*, 220*b*, 222*a*, and 222*b*. Wire collector 216 is generally planar or disk-shaped. It has a wire receiving means in the form of a central opening or passage 224 for receiving wires 218–222. Central opening 224 is defined by an inner peripheral sidewall 226*a*. The wire collector also has an outer sidewall 226*b*. While the inner and outer sidewalls have generally circular shapes, other shapes are also within the contemplation of the invention including polygonal and oval shapes. As in other embodiments, pairs of basket wires in this embodiment may be formed of a single of wire. In this regard, basket wires 218*a*–*b*, 220*a*–*b*, and 222*a*–*b*, respectively form three pairs, each of a single length of wire. Like wire collectors 16 and 116, wire collector 216 defines the separation point of the wires in each pair. In other words, it receives a length of wire going from a proximal end to a distal end and returns the wire from the distal end to the proximal end.

To collect and secure the wires using wire collector 216, wire collector 216 coordinates and implements an interlacing of wires. From a lower left side of wire collector 216, wire 220 is passed over sidewall 226 and then over an opposite side of sidewall 226. From a lower right side of wire collector 216, wire 218 is passed under sidewall 226 and over wire 220 in opening 224 and then under an opposite side of sidewall 226. Wire 222 passes under sidewall 226 and over wires 218 and 220 in opening 224 and then back under an opposite side of sidewall 226. This interlacing of wires braces the wires against each other and the wire collector, securing the distal tip of the basket. It can be seen that when wire 218 is added to the group of wires, it completes an interlacing arrangement, securing the distal end of the basket. It is additionally contemplated that the securing of interlaced or overlapped wires to a wire collector such as wire collector 216 could be effected by, for example, a short loop of wire that is not used to define the retrieval basket. Optionally, a bonding means such as a solder, adhesive, or other bonding agent could be applied to the junction of wires in the wire collector to better hold them together. It is also noted that an interlacing system could be based on a combination of structures. For example, another wire collector similar to wire collector 216 could fit within or around a wire collector 216 to help coordinate the interlacing of wires.

Advantageously, wire collector 216 allows a section of wire to define a predetermined shape of the distal end of basket 210 without extending beyond the predetermined basket shape. As can be seen, the wires are oriented in a substantially non-parallel relationship to the long axis of a basket. Accordingly, wire collector 216 provides a substantially tipless retrieval basket.

To better secure the wires, to maintain a smaller distal basket profile, and to maintain a desired wire separation, wire collector 216 may be provided with wire receiving means, such as grooved, notched, or similar regions for receiving and stationing the basket wires. Wires 218 and 222 entering and exiting from opening 224 from under sidewall 226 have receiving means 228*a*–*b* and 230*a*–*b*, respectively, disposed in inner sidewall 226*a*. Wire 220 entering and exiting from opening 224 from over sidewall 226 has receiving means 232*a*–*b* which comprise indentations on outer sidewall 226. The receiving means help maintain the position of the wires. A particular degree of wire separation of wires can be achieved by placing the wire receiving means at the desired points of separation along sidewall 226. Additional configurations of the foregoing embodiment are of course possible. For example, the present invention contemplates modifications in terms of the shape of the wire collector, the number of wires collected, and the spacing of wires.

Figure 12:
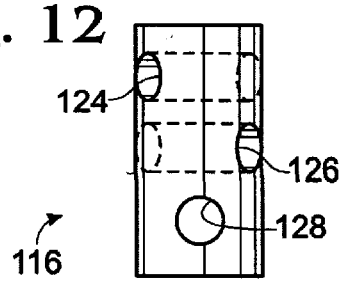
FIG. 12 shows a side elevation view of a wire collector for a six-wire basket according to the present invention.
Figure 13:
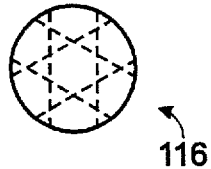
FIG. 13 shows a top elevation view of the wire collector of FIG. 12, with passages provided in the wire collector shown in phantom.
Figure 24:
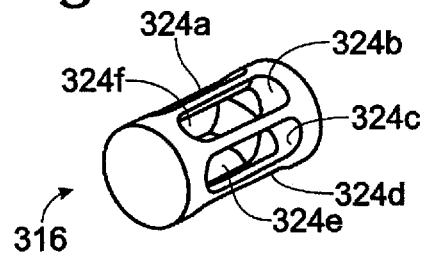
FIG. 24 shows a perspective view of an alternative embodiment of a wire collector according to the present invention.
Figure 25:
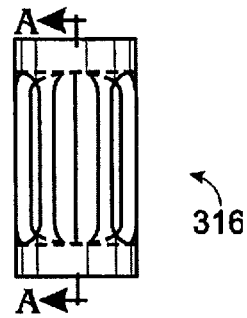
FIG. 25 shows a side elevation view of the embodiment of FIG. 24.
Figure 26:
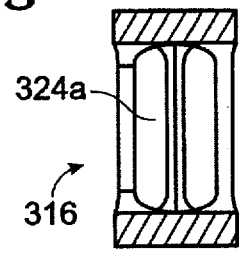
FIG. 26 shows a sectional view taken along line A—A in FIG. 25.
Figure 27:
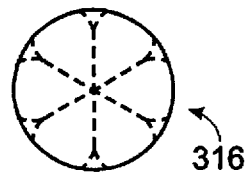
FIG. 27 shows a top view of the embodiment of FIG. 24.

Certain further embodiments consistent with the foregoing teachings are disclosed in FIGS. 24–27 and illustrate a six-wire basket somewhat similar to the embodiment of FIG. 12. In contrast to the passages in FIG. 12, which may closely match the diameter of a wire, the wire collector 316 of FIG. 24 provides a body with six openings or wire receiving means 324*a*–*f*. These openings are elongate or slotted in nature. The body of the wire collector 316 may be hollow, or semi-hollow, with the openings formed in the wall of the body for receiving and directing basket wires. As can be seen, there are three pairs of openings oppositely disposed in the body to facilitate these objectives. A length of wire is directed through one passage and out another passage. The length of wire is thereby providing two basket wires. This embodiment allows easier assembly of the wires because of the inclusion of the elongate passages. As an alternative to passing a wire through opposite openings, a wire may terminate in the hollow body. To retain the wire in the body of the wire collector, the wire may have a bulbous end disposed in the body of the wire collector so that it does not retract through the opening. The wire receiving means may also allow some movement of the wires to facilitate opening and closing of a basket formed of the wires. Accordingly, where such movement is provided by a wire receiving means, the wire receiving means also serves as a hinging means.

Figure 28:
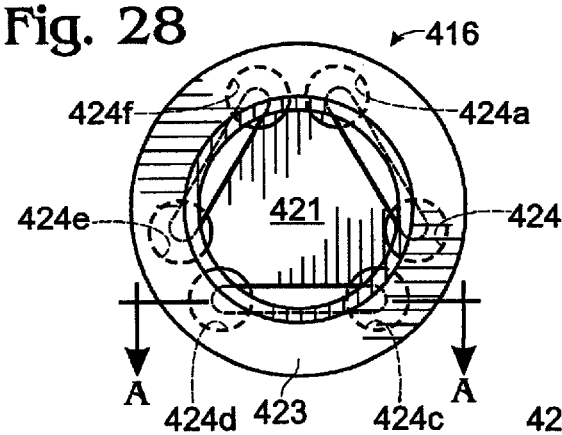
FIG. 28 shows a top view of another embodiment of a wire collector according to the present invention.
Figure 29:
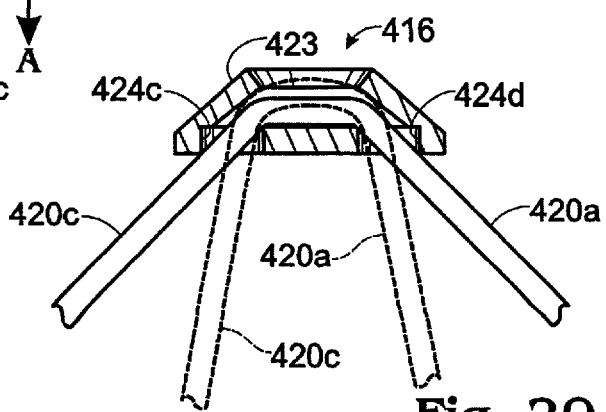
FIG. 29 shows a sectional view taken along line A—A in FIG. 28.

Another embodiment of a wire collector is shown in FIGS. 28–29. In this embodiment, the wire collector 416 comprises a generally planar body. Wire collector 416 includes a distally opposed flange 423. The wire collector includes wire receiving means in the form of six passages 424a–f for receiving wires to form a six-wire basket. The passages are disposed in pairs 424a–b, 424c–d, and 424e–f at or towards the periphery of the body. Preferably, the pairs are about equidistant from each other. Flange 423 may be perpendicular or angled relative to planar body 421. The relative angle of the flange may be adjusted to help direct and retain the wires running through the passages. To retain the wires, the flange may be swaged over the wires to secure them in place. The wires may also be soldered or welded in place or secured in place with a cap (not shown) that attaches or is integrated over the distal end of wire collector 416. FIG. 29 shows wires 420a and 420c running through the openings. As can be seen, the angle of a wire may match the flange's angle relative to planar body 421. As shown, the use of a planar body with wire passages results in a basket with essentially zero extending tip.

The wires are shown in an open-basket condition. The wire receiving means may allow some movement of the wires to facilitate opening and closing of a basket formed of the wires. The phantom lines show how the wires would appear in a closed-basket condition. Accordingly, where such movement or free-play is provided by a wire receiving means, the wire receiving means also serves as a hinging means allowing at least partial hinging of the wire.

Another embodiment of a wire collector 516 is shown in FIGS. 30–31. Although the body has a generally planar shape, the following features of this embodiment could also be implemented in other body shapes, including elongate bodies, spherical bodies, and bodies of other geometries. The wire collector consists of a generally planar body with a plurality of passages 524. The passages are disposed toward the periphery of the body. Preferably, the passages are about equidistant from each other. The passages are disposed in a proximal surface of the body of the wire collector and terminate into a wire anchor receiving means 525a–f for securing the ends of wires extending through passages 524 to the body of the wire collector. In the embodiment shown, an anchor receiving means consists of recesses 525a–f, each recess consisting of a region having expanded diameter or width relative to a passage 524. The anchor receiving means anchors a distal terminal end 527 of the wire 520 through an anchoring means disposed on a wire's terminal end. The anchoring means is a structure 527 which, through interaction with the anchor receiving means, precludes the wire from retreating proximally through its respective passage 524. Thereby, the wires are secured to the wire collector. In the embodiment of FIGS. 30 and 31, the wires 520a and 520d have an anchoring means 527 in the nature of a round terminal end that is generally of an complimentary size and shape relative to a recess 525a–f. The anchor thereby is seated in the recess and, because of its larger size relative to the passage 524, it cannot be retracted into the passage. Because it is too large to be withdrawn through passage 524, the anchor 527 secures the wire to the wire collector 516. (For simplicity, in FIG. 31 only two recesses are shown with a wire and anchoring means. In practice, each recess 525a–f would have a wire and anchoring means.) As a finish detail, the distal end of wire collector 516 could include a covering cap attached or integrated therewith.

As indicated in FIG. 31, the passages 524 in wire collector 516 may provide free-play for the wires (e.g., 520a, 520d) to move in a basket from a closed condition to an open condition (indicated in phantom). The wires are shown in a closed basket condition. The wire receiving means may allow some movement of the wires to facilitate opening and closing of a basket formed of the wires. The phantom lines show how the wires would appear in an open-basket condition. Accordingly, where such movement or free-play is provided by a wire receiving means, the wire receiving means also serves as hinging means.

In assembly, each wire could, for example, have a free end without anchoring means. The free end could be inserted through recesses 525 until the anchoring means at a wire's opposite end is disposed in the anchor receiving means. The anchoring means may be added to or formed on the wires before or after assembly to the wire collector. The anchors may be bonded to or formed in the wires using conventional techniques. For example, Nitinol wires may be swaged or laser welded to Nitinol anchors or swaged to stainless steel anchors. To retain the wires, the wire collector may be swaged or crimped over the wires to hold them in place. The wires may also be, for example, soldered or welded in place, or they may be secured in place with a cap (not shown) that attaches over the distal end of wire collector 516.

In addition to the example embodiments shown in FIGS. 30–31, the anchoring means may take on other arrangements and configurations. For example, the distal end of the wires could include anchoring means in the nature of a T-end that spans across an anchoring receiving means in the nature of a recess. Similarly, a "T" or other configuration could lock into anchor receiving means in the form of complementary notches or other complementary structure at the terminal end of a wire passage. Other such locking arrangements are certainly within the contemplation of this invention, but for the sake of brevity are not expressly described. The various wire collectors contemplated by the present invention may be made of any rigid or substantially rigid material including stainless steel, other metals and alloys thereof. It may also be made of synthetic materials including plastics, composites, etc., so long as the material selected is biocompatible. The wire collectors or parts thereof may be formed through milling, casting, extrusion and other processes known to persons skilled in the art.

FIGS. 32–34 show another possible embodiment of a wire collector 616 according to the present invention. The wire collector comprises a generally planar body with wire receiving means 624a and 624c for wires 620a and 620c, respectively (a corresponding third wire receiving means for wire 620b is present but not shown). More particularly, the body has a central portion 617 with three arms 619a, 619b and 619c extending therefrom. The arms are 120° apart. The wire receiving means are passages disposed in the terminal portion of each arm. Each wire 620a–b, 620c–d and 620e–f extends from a proximal portion of a basket, through a passage, and back to the proximal end of the basket. Thereby a single wire length forms two adjacent basket wires. The wires are shown in an open-basket condition. The wire receiving means may allow some movement of the wires to facilitate opening and closing of a basket formed of the wires. Accordingly, where such movement or free-play is provided by a wire receiving means, the wire receiving means also serves as hinging means. In the embodiment shown, the cross section of the wire may be circular so that wires move as a hinge within the receiving means to help the basket open and close. The wire collector may be made of stainless steel, with hinge-type joints formed on the body of the wire collector. By allowing hinging, the wire collector helps minimize bending stresses that occur during opening and closing of the basket.

A receiving means may be formed by providing a generally planar body with legs, and bending the legs around a fixture to form the receiving means. To facilitate construction of wire collector 616, it may be formed from a single piece or an assembly of two or more pieces. Pieces may be laser welded or affixed together using other known methods. It is also noted that central portion 617 and arms 619 may have other relative sizes and shapes. For example, central portion 617 could be minimized to form a three-spoke structure of substantially only the three arms.

FIG. 41 shows one possible variation of a wire collector with arms with wire receiving means. In this concept the wire collector has arms 819a–f with passages for receiving a terminal end of a wire. The passages are oriented generally perpendicular relative to the passages in wire collector 616.

Figure 42A:
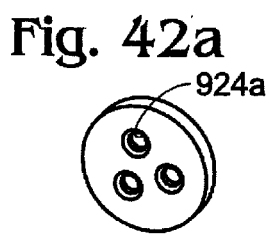
FIG. 42a shows a top perspective view of another embodiment of a wire collector according to the present invention.
Figure 42B:
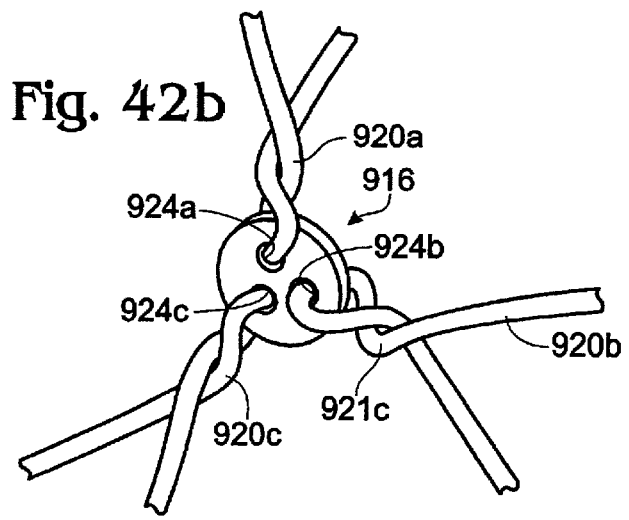
FIG. 42b shows the wire collector of FIG. 42a with wires.
Figure 43:
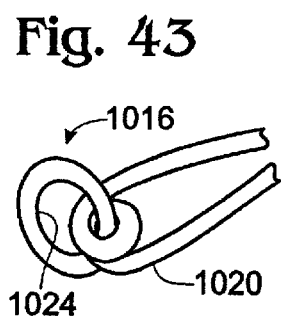
FIG. 43 shows a perspective view of another embodiment of a wire collector and wires according to the present invention.
Figure 44:
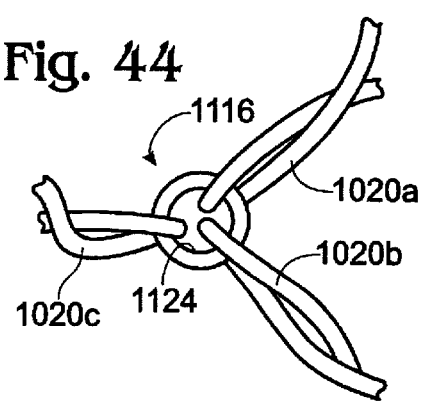
FIG. 44 shows a perspective view of another embodiment of a wire collector and wires according to the present invention.

FIG. 42 shows another embodiment of a wire collector 916 in accordance with the present invention. The wire collector comprises a generally planar body with three passages 924a–c. Each passage receives at least one length of wire 920a, b, c, respectively. Each wire enters a passage from one side of the planar body and exits the other. Accordingly, each wire length provides two basket wires. Just beyond where each basket wire extends from a passage, the wires are joined together to define a hinging means. In the example shown, the hinging means 921 is formed by twisting the opposite sections of wire together. The wire does not fit tightly within the passages, thereby basket wires may move angularly relative to the plane of the wire collector. FIGS. 43–44 show other embodiments of wire collectors and baskets similar to FIG. 42. In the case of these figures, wire collectors 1016, 1116 are substantially rigid, annular bodies, each providing a single, central passage 1024 or 1124 for accommodating a single or multiple wire lengths, respectively 1020 and 1120a–c. Different arrangements of twisting the wires to form hinging means are also illustrated. Although wire collector 1016 is shown holding only a single length of wire 1020 in central passage 1020, this is for simplicity of understanding. Additional wires may be accommodated by the passage.

The wires are shown in an open-basket condition. The wire receiving means may allow some movement of the wires to facilitate opening and closing of a basket formed of the wires. Accordingly, where such movement or free-play is provided by a wire receiving means, the wire receiving means also serves as hinging means.

Figure 45A:
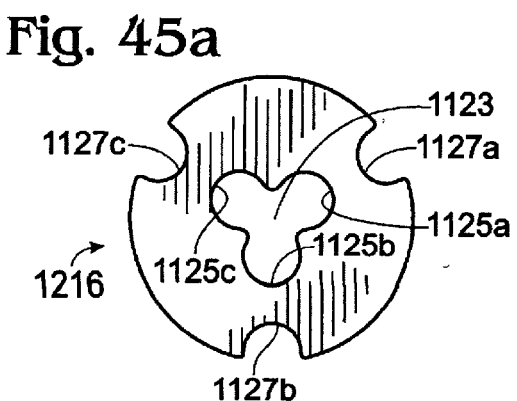
FIG. 45a shows a top view of still another embodiment of a wire collector according to the present invention.
Figure 45B:
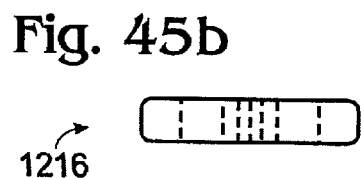

FIGS. 45–47 show another embodiment of a wire collector 1216 in accordance with the present invention. Wire collector 1216 generally planar or disk-shaped. As with other embodiments of the present invention, it is preferably a substantially rigid body. Wire collector 1216 has a central wire receiving means in the form of a central opening or passage 1123 for receiving wires. The central opening has a contoured shape to provide a plurality of wire receiving means 1125-a–c that act as grooves or pockets for securing a wire to the wire collector. While the wire receiving means are shown to have generally semicircular shapes, other shapes are also within the contemplation of the invention including curvilinear and rectilinear shapes that can receive a wire. There are also a plurality of wire receiving means 1127a–c along the outer circumference of the wire collector. Preferably, they are each aligned with a wire receiving means in the central passage. As in other embodiments, pairs of basket wires in this embodiment may be formed of a single wire placed through or around a wire receiving means. In this embodiment, a length of wire may be placed around each of wire receiving means 1125a–c, returning two basket wires 1129a–b to the proximal end of the basket formed with the wire collector. For illustrative purposes, FIGS. 46–47 show only a single wire in the wire collector. FIG. 46 shows an initial placement of a length of wire 1120 around wire receiving means 1127c. In FIG. 47, the wire length has been twisted so that there is a first crossover point 1132 adjacent wire receiving means 1127c. As a result of the cross over point, the wire forms a loop that closely wraps around the wire receiving means 1125c and 1127c. Preferably, the loop is not so tight that the wire cannot rotate or hinge around the sidewall of the wire collector. Such movement may facilitate the opening or closing of the basket for ingress or egress of calculi and other target bodies. Accordingly, where such movement is provided by a wire receiving means 1125 or 1127, the wire receiving means also serves as a hinging means.

Figure 48:
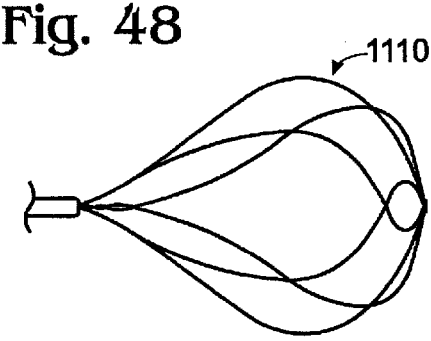
FIG. 48 shows a side view of a basket and shaft section according to the present invention.
Figure 49:
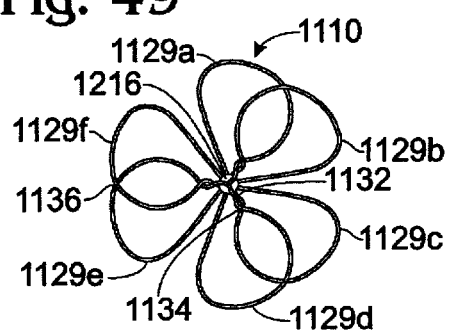
FIG. 49 shows a front view of the distal end of the basket of FIG. 48.
Figure 50:
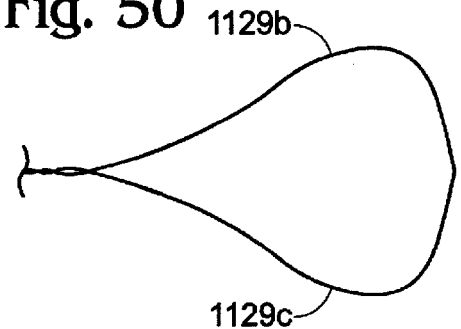
FIG. 50 shows a side of a first pair of wires in the basket of FIG. 48.
Figure 51:
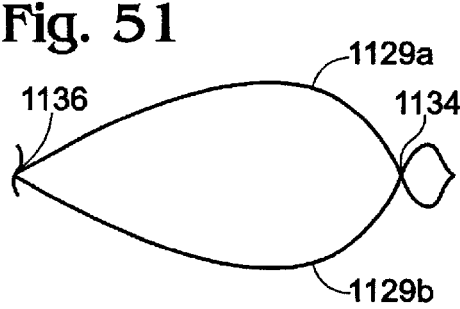
FIG. 51 shows a side of a second pair of wires in the basket of FIG. 48

As indicated the basket wires may have additional cross over points, for example, 1134 and 1136 going from the wire collector toward the proximal end of the basket. In between crossover points, the basket wires have points of maximum divergence from each other, with the wires converging on either side of the maxima to the cross over points. The wires may also be arranged so that there is an increasing degree of separation between the points of maximum divergence going from the wire collector to the proximal end of the basket. For example, $d_2$ is greater than $d_1$ in FIG. 47. Pairs of wires may move along opposite helical paths. In U.S. Pat. No. 6,187,017, certain such helical basket arrangements are disclosed that may be implemented using a wire collector according to the present invention. The '017 patent is hereby incorporated by reference in its entirety for all purposes. FIG. 48 shows a side view of a six-wire basket with wires 1129a–f formed using, for example, wire collector 1216. FIG. 49 shows a front view of the same basket. FIGS. 50–51 generally show two sets of basket wire pairs. FIG. 51 shows a pair of wires 1129a and 1129b that have crossovers 1134, and 1136, as indicated in FIG. 47. Pairs 1129c/1129d and 1129e/f are similarly arranged. Each basket wire in the pair extends proximally from the same receiving means, e.g., receiving means 1127c. Each such pair of basket wire pairs forms one of three lobes in the basket. Pair 1120b and 1120c are neighbor wires, that would reside on different receiving means 1127, without the cross over points indicated in FIG. 47.

For certain common urological procedures, wire collector 1216 is used to form a basket having a diameter of about 16 mm and length of about 26 mm. For a pair of basket wires formed from a length of wire, $d_1$ may be about 3 mm and $d_2$ about 9 mm. The wire collector may be made of stainless steel. It may be sized to receive wires of 0.006" diameter. The overall length of each basket wire may be about 33 mm. To facilitate retraction into a sheath, the wires may be placed closely adjacent at the proximal end of the basket, with a divergence point at about 4 mm. The foregoing is for illustrative purposes only. Persons skilled in the art will of course appreciate in view of the teachings herein that many variations are possible.

The present invention may be manufactured by known methods and equipment or adaptations of such that will be readily apparent to persons skilled in the art. One possible manufacturing method directed to the embodiment of FIG. 5 follows. Persons skilled in the art will appreciate how it may be used or adapted for other embodiments contemplated herein. FIG. 35 shows a side view of an apparatus used in making a basket according to the embodiment of FIG. 5. The apparatus includes a fixture 736 for receiving a basket formation fixture 738. In this example, the fixture 738 is in the nature of a removable plumb bob 738 and the fixture 736 has a complementary, funnel-like cavity. FIGS. 36 and 37 show a fixture having a plumb bob funnel 736 with a plurality of wire slots 740a–b, 742a–b and 743a–d. The plumb bob is splittable into a top half 741 and a bottom half 743 as shown in FIGS. 38–40. Referring back to FIG. 12, three wires of suitable length for forming a basket are inserted into a passage 124, 126, and 128 in a wire collector 116. A preferred wire is a Nitinol wire. After the wires are passed through a passage, the wire collector should have six wire legs of equal length. Looking at FIG. 36 the ends of each leg are each inserted through a slot 740a, 740b, 742a, 742b, 744a and 744b in funnel 736, creating a domed wire frame cavity on the funnel of 736. The slots are spaced in accordance with the desired spacing in the finished basket. Next, a splittable plumb bob 738 is inserted into the wire frame cavity. The plumb bob has the intended shape or profile of an open basket. The wire collector is centered on the apex 746 of plumb bob 738. The wires are inserted between pairs of alignment pins 748a–b, 750a–b, 752a–b disposed on the apex of the plumb bob. As indicated in FIG. 39, there are side grooves 754, 756 and 758 on the plumb bob for guiding a pair of wires from the wire collector along the side of the plumb bob. The alignment pins help orient the wires in their intended position in the finished basket. The wire ends extending downwardly through funnel 736 may now be inserted into a collar 13 below the plumb bob. The collar with wire ends is placed in a clamping device 760 disposed below funnel 736. The wire legs are then inserted through a wire guide tensioner 762. The free ends of the wires may be attached to a means for tensioning the wires around the plumb bob. For example, weights could be applied at the ends of the wires to exert a force that pulls the wires down and tight against the plumb bob. At this point the assembly may be inspected to ensure that the wires are in fact tight and properly aligned on the profile of the plumb bob. A helix may be formed in the basket wires by twisting means 764 (indicated in FIG. 35) for turning the distally collected wires a predetermined degree over the plumb bob while maintaining the proximal wire ends are static. In the embodiment of FIG. 6, the wires are twisted 90 degrees around the circumference of the plumb bob. At this point, the wires have the desired conformation of the basket. To set the conformation of Nitinol wires, and to impart desired shape memory, the wire and plumb bob assembly is processed with heat. Suitable conditions for a Nitinol wire are about 500° C. for about 20 minutes in an Argon furnace. After the heat processing, the assembly is removed from the furnace and water quenched. A suitable bonding agent such as an adhesive may be applied to the collar and/or wire collector to help secure the parts together and to seal the assembled parts. Ultraviolet light may be used to cure the adhesive, depending on the adhesive used. The wire legs may be braided to a desired pitch. The ends of the relaxed pitch shaft and the twisted wire shaft are soldered into the collar 13. The end of the twisted wire shaft may then may soldered or otherwise attached to its connection in the operating handle.

Figure 9A:
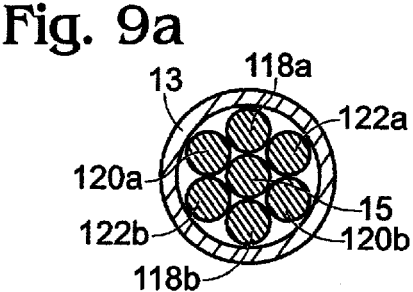
FIG. 9 shows a section of the device of FIG. 5 taken along line 9—9.
Figure 9B:
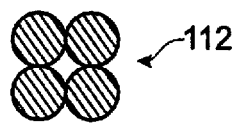

The manner in which baskets of the present invention may be joined to a shaft is discussed using the embodiments of FIGS. 5 and 12 as an example. Each wire loop 118, 120 and 122 has two ends that are coupled to the distal end of shaft 12 via a coupler 13. As shown in FIGS. 9a and 9b, one example of a coupler is a hollow collar that receives the distal end of the shaft and the ends of the wire loops. FIG. 9a is a cross section of the distal portion of collar 13 in which the ends of the basket wires are received. FIG. 9b is a cross section of the shaft 112 proximal to collar 13 in which the distal end of shaft 12 is received. In the example of FIG. 9b, the section of shaft 112 that proximally extends from collar 13 is formed of four wires in a relaxed pitch. In the shaft assembly shown, the collar 13 may be crimped at each end to secure the shaft and basket wires together. Alternatively, a basket and shaft may be secured together, with or without a coupler 13, by known bonding techniques such as soldering, welding, and/or chemical adhesives. Other means could also be used for coupling shaft 12 to a basket, including threaded connections, bonding agents, interference fits, and other known coupling or joining means.

One suitable construction of a shaft 12 is a small diameter wire or cable. In another possible embodiment, the shaft is formed from a plurality of wires twisted or otherwise congregated together. It is contemplated that the twisted wires may be the same as the wires forming the basket in which case no coupling means is necessary. Some or all portions of shaft 12 alternatively may be formed from a flexible monofilament, or a hollow or solid rod. Shaft 12 could also be formed of a combination of materials such as plastic-encased metal.

The basket or shaft materials may be made of known materials such as stainless steel, nickel-titanium alloys, or rigid thermoplastic materials.

As seen in FIG. 9, the shaft assembly may optionally include an elongate element 118. Elongate element 18 may run some or all of the length of shaft 12. The elongate element 118 would generally not extend beyond the distal end of shaft. The element may provide improved push or other structural or performance properties to the shaft, as desired. One example of an elongate element is a wire, rod or tube of the same or different diameter and/or material as a wire used to form the basket.

The wire collector may be used in conjunction with the inventions disclosed in U.S. Pat. No. 6,187,107 issued Feb. 13, 2001, entitled "Retrieval Basket for a Surgical Device", which is common owned by the assignee of the present application, and which is hereby incorporated by reference as if set forth herein in its entirety.

As noted above, the assembly of a retrieval basket and shaft would generally be used in combination with a sheath. The basket need not be fully retractable within the sheath. For example, it is contemplated that in certain embodiments the distal tip of the basket will have a larger width or diameter than the inner diameter of the sheath of that there is an interference fit, thereby the basket may be fully enclosed within the sheath but not retractable beyond its distal end. FIGS. 14-19 illustrate the use of a sheath 14 with a retrieval basket. The sheath may be the same or similar to sheaths used in conventional retrieval basket devices. Suitable materials for constructing the sheath include polyimide and/or PTFE. For many minimally invasive surgical procedures, a suitable outside diameter of the sheath will be in the range of about 0.04–0.06 inch. The sheath will have an inner diameter sufficient to allow passage of the basket/shaft assembly (approximately 0.034"–0.05" inner diameter). The outside and inside diameters of sheath 14 could be larger or smaller. Preferably, wire collectors 16 and 116 are adapted to slidably retract within a sheath 14. However, the wire collector could be made to stop adjacent the distal opening of the sheath, and not be fully retractable therewithin. For example, the wire collector could be sized so that it has an outer diameter that is greater than the inner diameter of the sheath. The outer diameter of the wire collector should not be so great that it will not fit within the endoscope channel used to deliver the basket to a surgical site. The sheath is preferably semi-rigid in its proximal portion with increased flexibility in its distal portion for suitable scope deflection and basket placement, especially in the lower pole calyx. The external sheath may be coated with a known lubricious hydrogel that becomes hydrophilic when wetted so as to ease passage of the sheath through an instrument, or basket assembly through the sheath.

Figure 14:
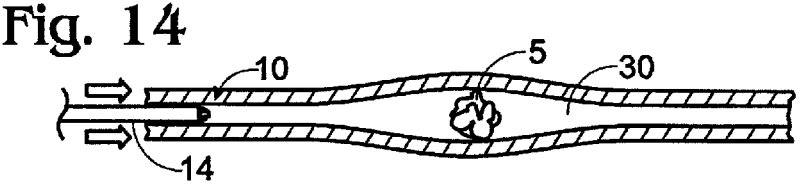
FIG. 14 shows a sheathed basket being advanced in a body channel toward a target body, as the first in a sequence of actions depicted in FIGS. 14–19 that capture and retract the target body.
Figure 15:
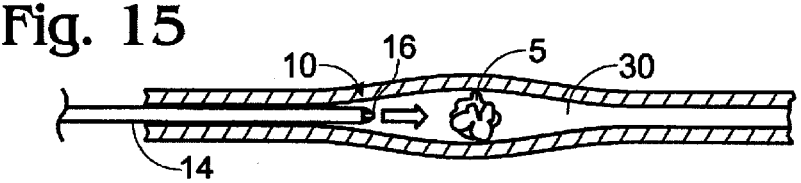
FIG. 15 shows the basket of FIG. 14 being further advanced toward the target body.

As shown in FIGS. 14–19, a sheath 14 can be movably positioned relative to at least portions of shaft 12 and basket 10 to provide means for alternating the basket between a closed, retracted position and a deployed, expanded position. More particularly, FIGS. 14–19 show how basket 10 captures a target body 5 depending on a sequence of actions taking the basket from a closed retracted position to a deployed, expanded position and then back to a retracted position. In this example, the basket is a helical wire basket. It will be understood by persons skilled in the art that a sheath and retrieval basket device system may be introduced into a body channel by means of a lumen in an endoscope. The endoscope would include optical components to facilitate positioning and use of the device in a body channel. In FIGS. 14 and 15, sheath 14 holds a retracted basket 10.

Figure 16:
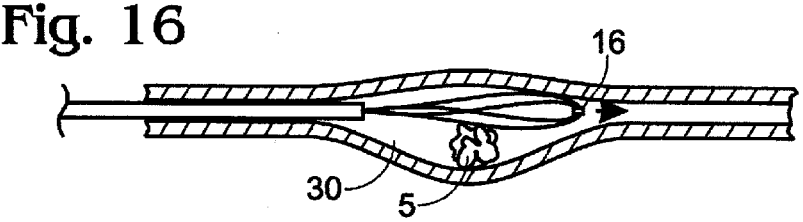
FIG. 16 shows the basket positioned near the target body with the basket being deployed out of the sheath and beyond the target body.
Figure 17:
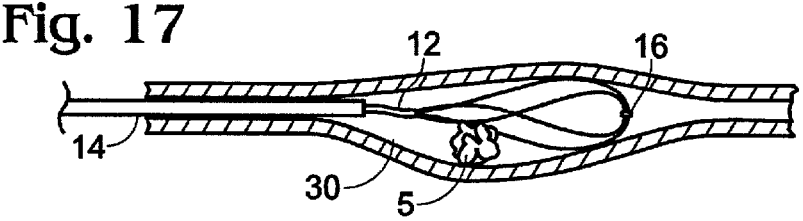
FIG. 17 shows the fully deployed and expanded basket being positioned for stone ingress.
Figure 18:
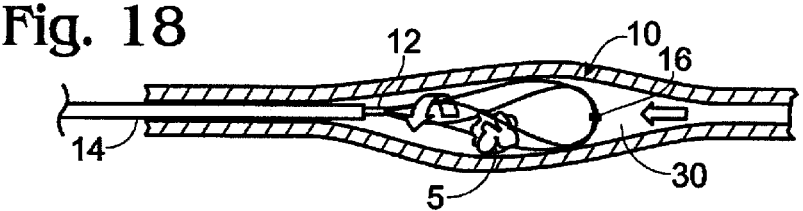
FIG. 18 shows the basket being rotated and retracted to capture the target body.
Figure 19:
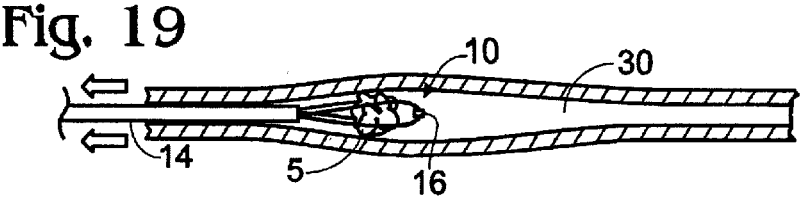
FIG. 19 shows the basket closed around the target body, capturing it, with the basket more fully retracted toward the sheath and the sheath being retracted from the body channel.

The sheathed basket is being advanced into a body channel 30, such as the ureter, toward a target body 5, such as a stone. In the case of removal of a stone from the ureter, the retrieval basket could be used with a ureteroscope, which includes a lumen for the retrieval basket device system. Just short of the target body 5, basket 10 is extended from sheath 14 beyond the target body, as seen in FIG. 16. The basket expands, dilating the body channel. FIG. 17 shows the fully deployed and expanded basket being positioned for stone ingress. The basket and sheath are dragged proximally, engaging the target body. Turning to FIGS. 18 and 19, based on the helical arrangement of the wires in the basket, as basket 10 is retracted into sheath 14 there is a camming action between the basket wires and the inner diameter at the distal end opening of sheath 14. This produces a helical rotational effect in the basket, with the basket wires converging helically toward a longitudinal axis of the basket. As the basket closes in this manner, target body 5 is drawn to the center of the basket and captured there. The basket retrieval device system, captured target body, and ureteroscope may then be withdrawn from the patient's body.

FIG. 20 shows an example of a basket 10 being positioned to remove a lower pole calyx stone 5 from a kidney 32. Basket 10 includes a wire collector 16 that has little or no extending tip. To access the kidney calyx, the basket device may be passed through a ureteropyeloscope. As seen in FIG. 20, the device may be maneuvered through tortuous and narrow body areas where the only basket ingress for a target body is at the distal tip of the basket. Because conventional devices have a substantial standoff distance between the basket distal end and the extending tip, it would be impossible or very difficult to remove an impacted target body from a kidney as shown. In contrast, in the present invention, the distal end of basket 10 may be constructed to have little or no standoff distance. Therefore, it may be positioned against the kidney tissue where target body 5 is impacted to capture the target body within basket 10.

FIG. 21 shows the retrieval of an impacted target body 5, e.g., a stone, from a vessel, e.g., a ureter. Basket 10 is deployed from a sheath adjacent the stone. The stone may be plucked from the ureter wall by rotating the device handle, causing the basket wires to slip behind the stone. The basket may then be retracted. Round basket wires are preferred for this procedure to reduce the risk of trauma during contact of the basket with the ureteral walls. Although a tipless basket is not necessarily required for the procedure of FIG. 21, sometimes the procedure of FIG. 20 is concurrently performed where a conventional basket with a tip may not reach the stone because of the tip standoff distance. Even where standoff distances are not an issue, a wire collector improves the performance of a basket because it adds rigidity to the basket structure so that the basket may be maneuvered past obstacles such as a stone. The wire collector also improves basket integrity, enabling better dilation of a body passage such as the ureter.

Looking again at the four-wire basket 10 and the six-wire basket 110, certain relative advantages of each will be noted. With fewer wires, a four-wire basket can achieve a smaller outer diameter. A smaller outer diameter will take up less room in a channel of an endoscope leaving room in the endoscope for other utilities or functions, such as irrigation. The four-wire basket has more spacing between wires for ingress of larger stones. Since fewer wires are used, the basket is longitudinally less rigid, making it more deformable and maneuverable around obstacles. In contrast, a six-wire basket is better suited for extraction of smaller stones. The wires are more closely spaced, leading to better retention of smaller stones. The additional wires also provide relatively greater radial force for dilating a ureter, for example. Further, the additional wires provide relatively greater rigidity for moving past a tight or obstructed area.

The handle and shaft components of a surgical device are not critical to this invention and the handle and shaft components described herein can be interchanged with equivalent or conventional components. Handles/controls known to those skilled in the art may also be incorporated. Suitable handle and shaft arrangements are known and marketed as part of the SURLOK™ Flat-Wire Stone Basket and SURLOK™ Helical Stone Baskets provided by Circon Corporation of Santa Barbara, Calif. Additional assemblies are described in Dormia, U.S. Pat. No. 4,347,846, Bates et al., U.S. Pat. No. 5,496,330 and Fleury et al., U.S. Pat. No. 5,573,530, each of which are incorporated herein by reference in their entireties. One handle base/slider assembly embodiment comprises a handle base with a slide, which attaches to a connector tube and manipulates the shaft-basket assembly so as to deploy and retract the basket out of and back into the sheath. Another handle base/slider assembly embodiment comprises a handle base with a slider, which is attached to the external sheath so as to manipulate the sheath off of and back onto the basket. A handle may include a movable thumb slide basket positioner that is connected to a cable that extends to the basket. The thumb slide permits the advancement and retraction of the basket with respect to the handle. A sheath is fixedly attached to the handle and remains stationary with respect to the handle. Advancement of the basket by means of the thumb slide in the distal direction causes the basket to extend from the end of the sheath so that it expands. Retraction of the thumb slide in the proximal direction retracts the basket into the end of the sheath. Alternatively, the handle can include a mechanism for positioning a movable sheath, and the basket can be fixed with respect to the handle. In such a configuration, advancement of the moveable sheath collapses the basket and retraction of the sheath allows the basket to expand.

While the invention is generally described in terms of a device for the removal of calculi from the urinary tract of a patient, it is contemplated that other surgical instruments and other applications would benefit from the invention.

What we claim:

1. A medical retrieval basket, comprising:
   a plurality of basket wires forming a basket;
   a wire collector, with means for receiving each basket wire, disposed at a distal end of the basket, the wire collector comprising a substantially rigid body and receiving the wires so as to provide a substantially tipless basket.

2. The basket of claim 1 wherein the means for receiving each basket wire receive the basket wires and orient them in a manner that is substantially non-parallel to the long axis of the basket when the basket is in the open position.

3. The basket of claim 2 wherein the wires are received in an orientation that is generally perpendicular to the long axis of the basket.

4. The basket of claim 1 wherein the body is a substantially solid body.

5. The basket of claim 1 wherein the body is substantially hollow.

6. The basket of claim 4 wherein the receiving means comprise passages in the body.

7. The basket of claim 1 wherein a passage extends from one opening in the body to another opening so that a length of wire may pass therethrough and form two basket wires.

8. The basket of claim 7 wherein the basket wires extend from the body in an orientation generally transverse to the long axis of the basket when the basket is in its open position.

9. The basket of claim 1 wherein the wire collector and the wires are integrally formed of the same material.

10. The basket of claim 1 wherein the collector has a generally planar body.

11. The basket of claim 10 wherein the planar body has a central opening for receiving basket wires.

12. The basket of claim 1 wherein the basket wires terminate in the body.

13. The basket of claim 2 wherein the basket wires terminate in the body.

14. The basket of claim 1 wherein the basket wires terminate in anchor receiving means provided in the body and the terminal ends of the wires include anchoring means.

15. The basket of claim 1 further comprising a shaft attached to the proximal end of the basket.

16. The basket of claim 15 further comprising a sheath into which the shaft is slidably disposed.

17. A medical retrieval basket, comprising:
    a plurality of basket wires forming a basket;
    a wire collector, with receiving means for receiving basket wires, disposed at a distal end of the basket, the wire collector comprising a substantially rigid body, the receiving means receiving the wires in an orientation that is substantially non-parallel to a long axis of the basket when the basket is in its open position.

18. The basket of claim 17 wherein the wires are received in an orientation that is generally perpendicular to the long axis of the basket.

19. The basket of claim 17 wherein the body is a substantially solid body.

20. The basket of claim 17 wherein the body is substantially hollow.

21. The basket of claim 17 wherein the body is an elongate substantially solid body.

22. The basket of claim 17 wherein the receiving means comprise passages in the body.

23. The basket of claim 22 wherein a passage extends from one opening in the body to another opening so that a length of wire may pass therethrough and form two basket wires.

24. The basket of claim 23 wherein the basket wires extend from the body in an orientation generally perpendicular to the long axis of the basket when the basket is in its open position.

25. The basket of claim 17 wherein the wire collector and the wires are integrally formed of the same material.

26. The basket of claim 17 wherein the collector has a generally planar body.

27. The basket of claim 26 wherein the generally planar body has a central opening for receiving basket wires.

28. The basket of claim 17 wherein the basket wires terminate in the body and wherein the wires are helically oriented.

29. The basket of claim 24 wherein the basket wires terminate at terminal ends in the body.

30. The basket of claim 29 wherein the basket wires terminate in anchor receiving means provided in the body and the terminal ends of the wires include anchoring means.

31. The basket of claim 17 further comprising a shaft attached to the proximal end of the basket.

32. The basket of claim 31 further comprising a sheath into which the shaft is slidably disposed.

33. A medical retrieval basket, comprising:
    a plurality of basket wires forming a basket, the wires being formed of a shape-memory material;
    a shaft extending proximally of the basket; and
    a wire collector, with receiving means for receiving basket wires, disposed at a distal end of the basket, the wire collector comprising a substantially rigid body, the receiving means receiving the wires in an orientation that is substantially non-parallel to a long axis of the basket when the basket is in its open position.

34. The basket of claim 33 wherein the wires are received in an orientation that is generally perpendicular to the long axis of the basket.

35. The basket of claim 33 wherein the body is a substantially solid body.

36. The basket of claim 33 wherein the body is substantially hollow.

37. The basket of claim 33 wherein the body is an elongate substantially solid body.

38. The basket of claim 33 wherein the receiving means comprise passages in the body.

39. The basket of claim 38 wherein a passage extends from one opening in the body to another opening so that a length of wire may pass therethrough and form two basket wires.

40. The basket of claim 39 wherein the basket wires extend from the body in an orientation generally perpendicular to the long axis of the basket when the basket is in its open position.

41. The basket of claim 33 wherein the wire collector and the wires are integrally formed of the same material.

42. The basket of claim 33 wherein the collector has a generally planar body.

43. The basket of claim 42 wherein the generally planar body has a central opening for receiving basket wires.

44. The basket of claim 33 wherein the basket wires terminate in the body.

45. The basket of claim 40 wherein the basket wires terminate in the body.

46. The basket of claim 45 wherein the basket wires terminate in anchor receiving means provided in the body and the terminal ends of the wires include anchoring means.

47. The basket of claim 46 further comprising a sheath into which the shaft is slidably disposed.

48. A medical retrieval basket, comprising:
a plurality of basket wires forming a basket, the basket wires comprising a shape-memory material;
a wire collector, with means for receiving basket wires, disposed at a distal end of the basket, the wire collector comprising a substantially rigid body and receiving the wires so as to provide a substantially tipless basket.

49. The basket of claim 48 wherein the wire collector comprises a body with a plurality of passages that receive the basket wires.

50. The basket of claim 48 wherein the wire collector defines a substantially hemispherically shaped distal basket portion.

51. The basket of claim 48 wherein the basket has at least two pair of wires that follow helical paths.

52. The basket of claim 49 wherein the passages run generally transverse to the longitudinal axis of the basket.

53. The basket of claim 48 wherein the basket has at least two pair of wires that follow helical paths, the wires extending from the wire collector in a substantially non-parallel orientation relative to the longitudinal axis of the basket.

54. The basket of claim 48 wherein the wire collector is formed on and encases a junction of wires comprising the distal end of the basket, securing the wires together in a desired arrangement.

55. The basket of claim 54 wherein the wire collector is formed of a bonding agent comprising an epoxy.

56. The basket of claim 48 wherein the body is generally cylindrical in shape.

57. The basket of claim 48 wherein the body has at least three passages.

58. The basket of claim 48 wherein the wire collector includes a central opening, the wires being interlaced using the central opening of the wire collector to form a distal end of the basket.

59. The basket of claim 58 wherein a first wire traverses the central opening on one side of the wire collector, a second wire traverses the wire collector on an opposite side of the central opening, the first and second wires crossing each other in the opening, and a third wire traverses the opening from the same side of the wire collector as the first or second wire and crosses over the first and second wires in the opening so as to secure all wires together.

60. The basket of claim 58 wherein the wire collector includes one or more wire receiving means on an inner or outer sidewall of the body of the wire collector.

61. The basket of claim 59 wherein the wire receiving means comprises notches formed in a sidewall of the wire collector.

62. The basket of claim 58 wherein a bonding agent is disposed over the interlaced wires to help secure the wires together.

63. The basket of claim 58 wherein at least a pair of basket wires follow helical paths.

64. A medical retrieval basket device, comprising:
a plurality of basket wires forming a basket for capturing a target body and a shaft attached proximally thereto, the basket including a wire collector at its distal end, the wire collector comprising a body having a plurality of wire receiving means that help define a shape of at least a distal portion of the basket; at least two basket wires forming a pair extending along helical paths, the pair of wires being closely spaced and adjacent in a proximal region of the baskets, radially diverging in an intermediate region of the basket, and radially converging in a distal region of the basket into the wire collector.

65. The basket of claim 64 wherein a wire passes through a passage in the wire collector and is returned to a proximal end of the basket.

66. The basket of claim 64 wherein the distal end of the basket and a distal end of the body of the wire collector are substantially coextensive.

67. The basket of claim 64 wherein the wire collector defines a substantially tear-drop shaped basket.

68. The basket of claim 64 wherein the body has at least three passages for receiving wires, a first passage lies above a second passage, which lies above a third passage, each passage being offset from another passage, and each passage defining a wire return path that allows a wire to return to a proximal end of the basket.

69. The basket of claim 64 wherein a basket wire has a proximal portion and a distal portion, wherein the basket wire's radius of curvature in the proximal basket portion is greater than its radius of curvature in the distal portion.

70. A medical device that includes a basket device and sheath, the basket device being retractable into the sheath, the basket device comprising:
a plurality of basket wires forming a basket, the basket including a wire collector at its distal end, the wire collector comprising a body receiving and securing basket wires at the distal end of the basket so as to provide a substantially tipless basket, wherein the wires have a substantially round cross section.

71. A method of forming a basket for a retrieval basket comprising:
providing a wire collector having a plurality of wire receiving means;
placing wires in the plurality of wire receiving means; and
providing a form representing a desired basket shape, the form including positioning means for setting the wires in a predetermined position; arranging wires around the form; fixing one or both ends of the wires in the basket so that they are secured together and define a basket; and removing the form.

72. The basket of claim 71 wherein the positioning means comprises a plurality of grooves spaced a predetermined distance from each other and having a predetermined depth.

73. A form representing a desired retrieval basket shape, the form having wire positioning means for receiving and setting a plurality of basket wires in a predetermined position, the form including means for receiving and positioning a wire collector.

74. The form of claim 73 wherein the positioning means comprises grooves spaced a predetermined distance from each other and having a predetermined depth.

75. The form of claim 73 wherein the form represents a basket having a substantially hemispherically shaped distal portion.

76. The form of claim 73 wherein the form represents a basket having a cone-shaped proximal portion.

77. The basket of claim 2 wherein the wire collector includes hinging means allowing movement of wires at the wire collector and hereby facilitating opening and closing of a basket formed using the wire collector.

78. The medical device of claim 17 wherein the wire collector includes hinging means for allowing movement of wire at the wire collector and thereby facilitating opening and closing of a basket formed using the wire collector.

79. The basket of claim 77 wherein the hinging means comprise the wire receiving means.

80. The medical device of claim 78 wherein the hinging means comprises the wire receiving means.

81. The basket of claim 79 wherein the wire receiving means comprises a notched area in a substantially planar body.

82. The medical device of claim 80 wherein the wire receiving means comprises a notched area in a substantially planar body.

83. A medical retrieval basket, comprising:
   a plurality of basket wires forming a basket;
   a wire collector, with means for receiving basket wires, disposed at a distal end of the basket, the wire collector comprising a substantially rigid, generally planar body, the body receiving the wires so as to provide a substantially tipless basket.

84. The medical retrieval basket of claim 83 wherein the body has wire receiving means for receiving wires comprising notches in a sidewall of the body.

85. The medical device of claim 84 wherein the body is a generally annular shaped body with a central opening, the notches being disposed around the sidewall of the body.

86. The medical device of claim 84 wherein the wire receiving means is also a hinging means.

87. The medical device of claim 84 wherein there are at least two wire receiving means, two or more basket wires extending proximally from each receiving means.

88. The medical device of claim 87 wherein a pair of basket wires are formed from a single length of wire having a cross-over point adjacent a receiving means.

89. The medical device of claim 88 wherein the cross-over point defines a section of wire hingeably disposed around the receiving means.

* * * * *